(12) United States Patent
Conley et al.

(10) Patent No.: US 8,906,075 B2
(45) Date of Patent: Dec. 9, 2014

(54) METHODS AND ASSEMBLIES FOR ALIGNING A BONE FIXATION PLATE

(75) Inventors: Jordan Conley, West Chester, PA (US); Andre Galm, Solothurn (CH); Fabian Jaeggi, Solothurn (CH)

(73) Assignee: DePuy Synthes Products, LLC, Raynham, MA (US)

( * ) Notice: Subject to any disclaimer, the term of this patent is extended or adjusted under 35 U.S.C. 154(b) by 109 days.

(21) Appl. No.: 13/182,505

(22) Filed: Jul. 14, 2011

(65) Prior Publication Data

US 2012/0265253 A1      Oct. 18, 2012

Related U.S. Application Data

(60) Provisional application No. 61/364,232, filed on Jul. 14, 2010.

(51) Int. Cl.
 *A61B 17/80* (2006.01)
 *A61B 17/86* (2006.01)

(52) U.S. Cl.
 CPC ........... *A61B 17/808* (2013.01); *A61B 17/8057* (2013.01); *A61B 17/8605* (2013.01); *A61B 17/8061* (2013.01)
 USPC .......................................... 606/286; 606/282

(58) Field of Classification Search
 USPC ................. 606/280, 281, 282, 286
 See application file for complete search history.

(56) References Cited

U.S. PATENT DOCUMENTS

| | | | |
|---|---|---|---|
| 1,105,105 A | 7/1914 | Sherman | |
| 2,526,959 A | 10/1950 | Lorenzo | |
| 4,388,921 A | 6/1983 | Sutter et al. | |
| 5,006,120 A | 4/1991 | Carter | |
| 5,015,248 A | 5/1991 | Burstein et al. | |
| 5,201,733 A | 4/1993 | Etheredge, III | |
| 5,433,719 A | 7/1995 | Pennig | |
| 5,569,248 A | 10/1996 | Matthews et al. | |
| 5,601,553 A | 2/1997 | Trebing et al. | |
| 5,676,667 A * | 10/1997 | Hausman | 606/281 |
| 5,690,633 A | 11/1997 | Taylor et al. | |
| 5,709,686 A | 1/1998 | Talos et al. | |
| 5,709,687 A | 1/1998 | Pennig | |
| 5,766,175 A | 6/1998 | Martinotti | |
| 5,968,046 A | 10/1999 | Castleman | |
| 5,989,255 A | 11/1999 | Pepper et al. | |

(Continued)

FOREIGN PATENT DOCUMENTS

| | | |
|---|---|---|
| DE | 3942326 | 6/1991 |
| DE | 10319781 | 8/2004 |

(Continued)

OTHER PUBLICATIONS

"VariAx™ Distal Radius Locking Plate System", Stryker®, © 2009, 12 pages.

(Continued)

*Primary Examiner* — Andrew Yang
(74) *Attorney, Agent, or Firm* — Baker & Hostetler LLP

(57) ABSTRACT

A bone fixation assembly is provided, including a bone fixation plate that has a plurality of apertures having different cross-sectional dimensions, and a temporary fixation wire. The temporary fixation wire includes an abutment member that can compress the bone fixation plate against an underlying bone so that the alignment of the bone fixation plate on the bone can be analyzed prior to using bone fixation members to permanently attach the bone fixation plate to the underlying bone.

34 Claims, 7 Drawing Sheets

(56) References Cited

U.S. PATENT DOCUMENTS

| | | |
|---|---|---|
| 6,375,657 B1 | 4/2002 | Doubler et al. |
| 6,648,891 B2 | 11/2003 | Kim |
| 6,875,215 B2 | 4/2005 | Taras et al. |
| 7,517,350 B2 | 4/2009 | Weiner et al. |
| 7,641,677 B2 | 1/2010 | Weiner et al. |
| 2004/0059335 A1 | 3/2004 | Weaver et al. |
| 2004/0097941 A1 | 5/2004 | Weiner et al. |
| 2005/0085818 A1* | 4/2005 | Huebner ............ 606/69 |
| 2007/0208378 A1 | 9/2007 | Bonutti et al. |
| 2007/0225716 A1 | 9/2007 | Deffenbaugh et al. |
| 2007/0276402 A1 | 11/2007 | Frankel et al. |
| 2008/0065070 A1 | 3/2008 | Freid et al. |
| 2009/0036933 A1 | 2/2009 | Dube et al. |
| 2009/0099610 A1 | 4/2009 | Johnson et al. |
| 2009/0216242 A1 | 8/2009 | Riemer et al. |
| 2009/0281543 A1 | 11/2009 | Orbay et al. |

FOREIGN PATENT DOCUMENTS

| | | |
|---|---|---|
| DE | 102004009429 | 9/2005 |
| DE | 202008000914 | 3/2008 |
| DE | 202007017159 | 5/2008 |
| EP | 0506420 | 9/1992 |
| EP | 1878394 | 1/2008 |
| WO | WO 97/20514 | 6/1997 |
| WO | WO 03/057055 | 7/2003 |

OTHER PUBLICATIONS

"The New Comprehensive Stryker® VariAx™ Distal Radius Locking Plate System", © 2009, 20 pages.

Technique Guide: 2.4 mm Variable Angle LCP Distal Radius System. Synthes, 2008, 43 pages.

* cited by examiner

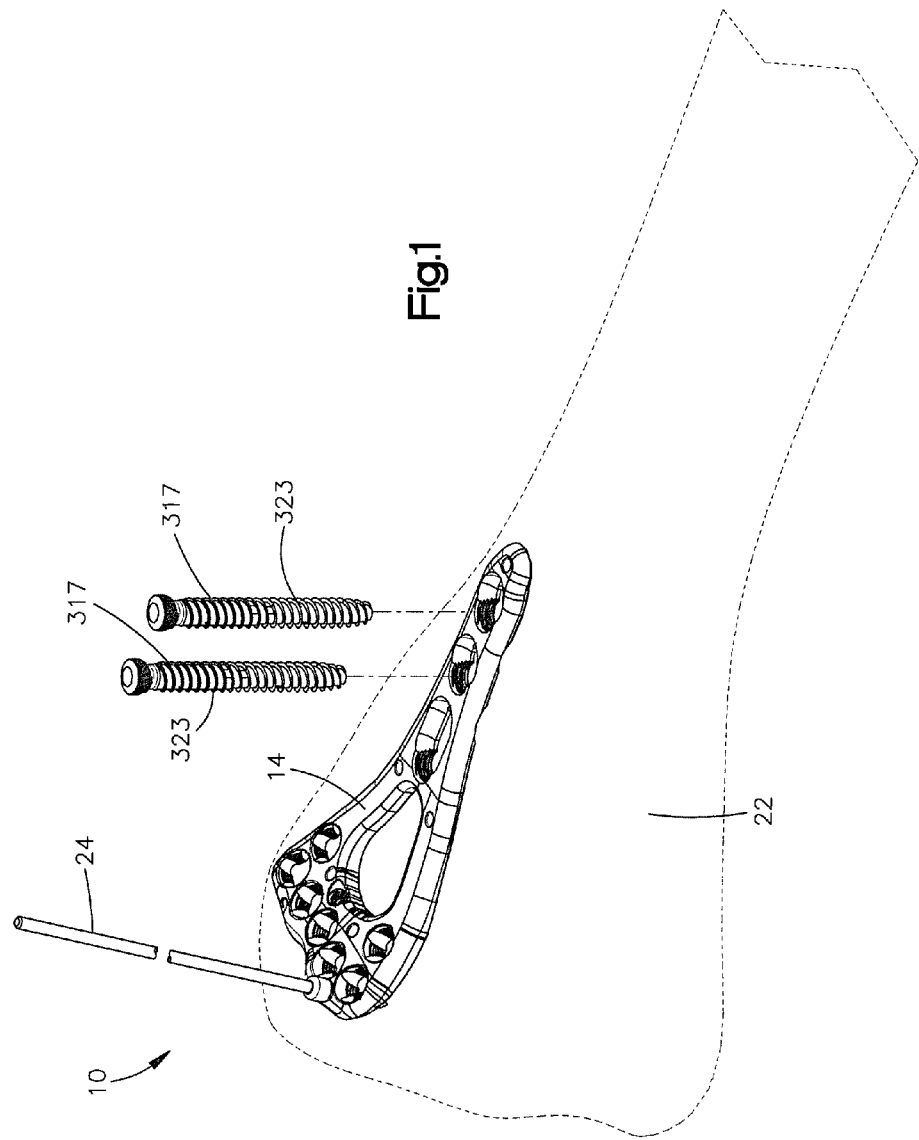

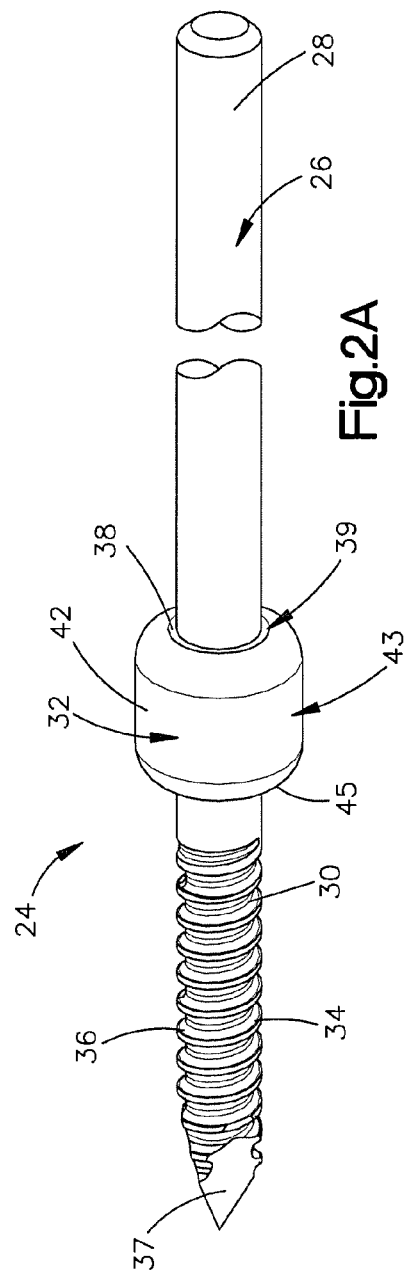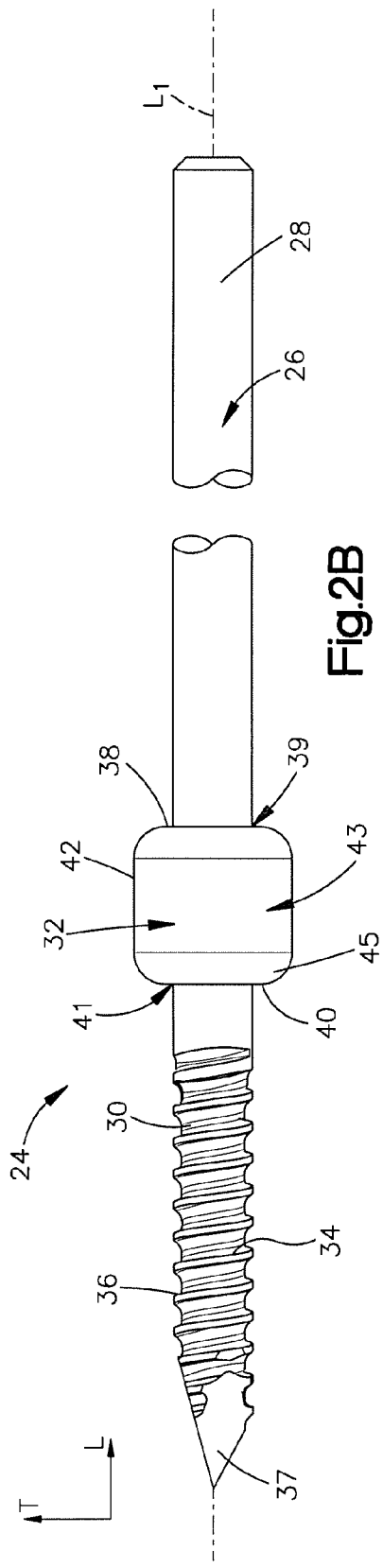

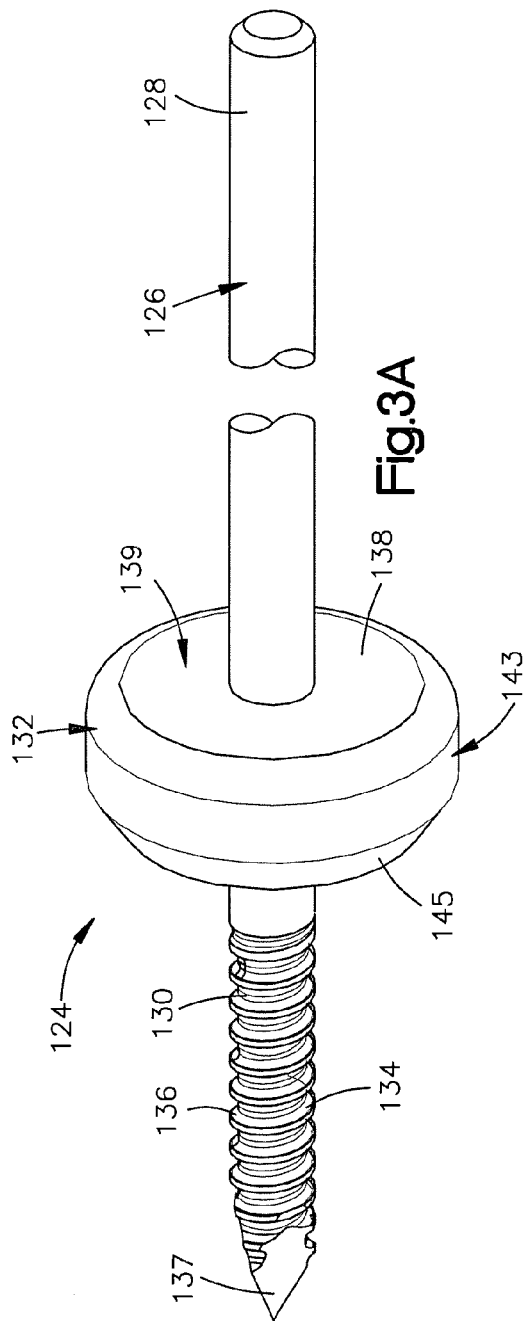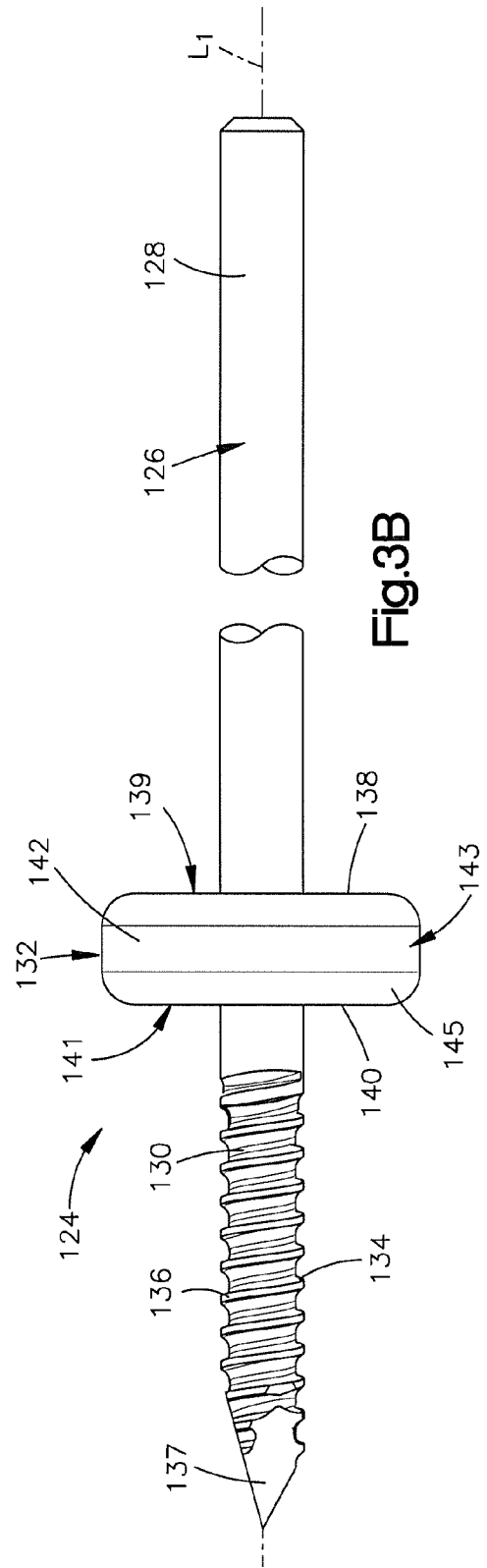

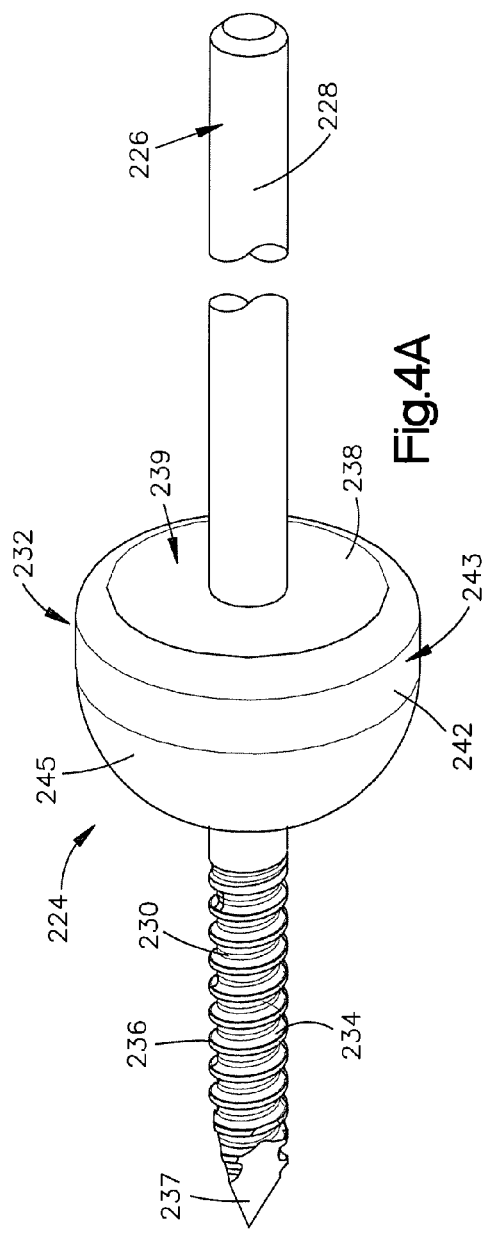
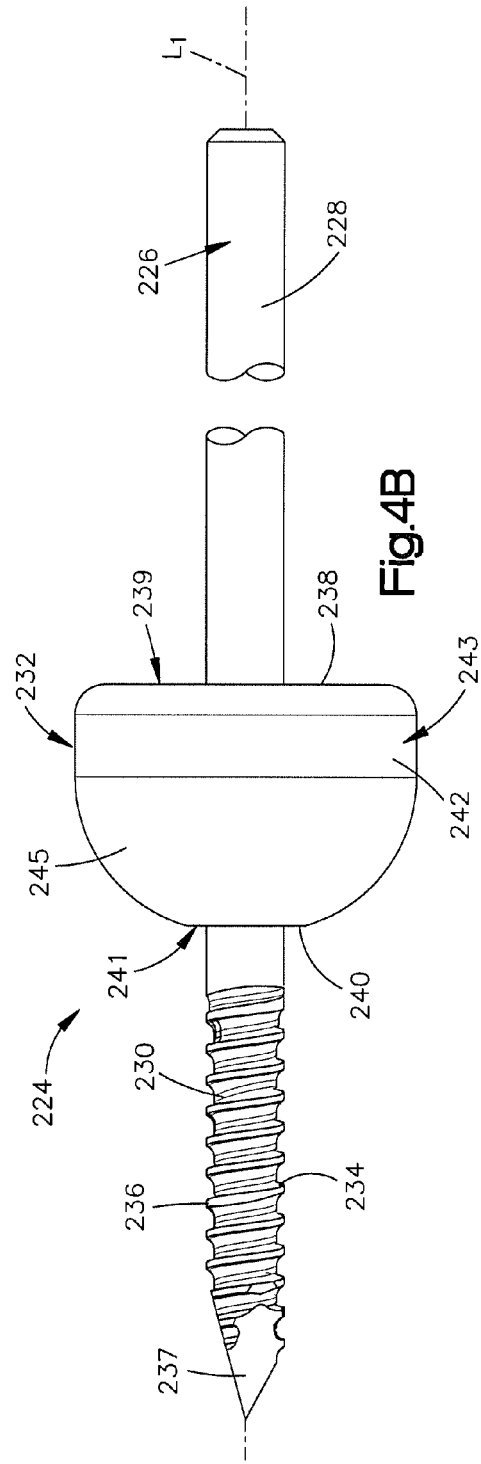

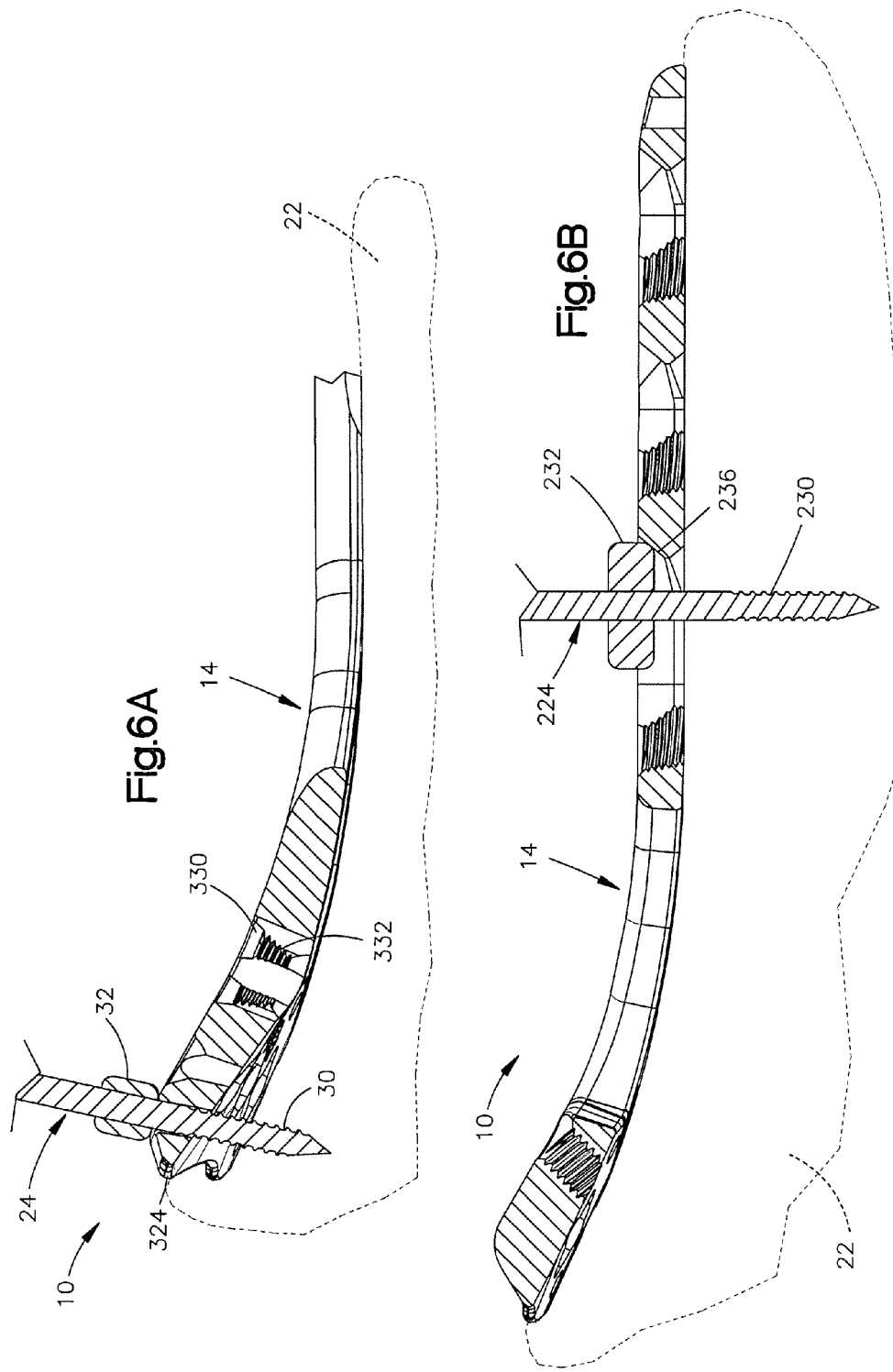

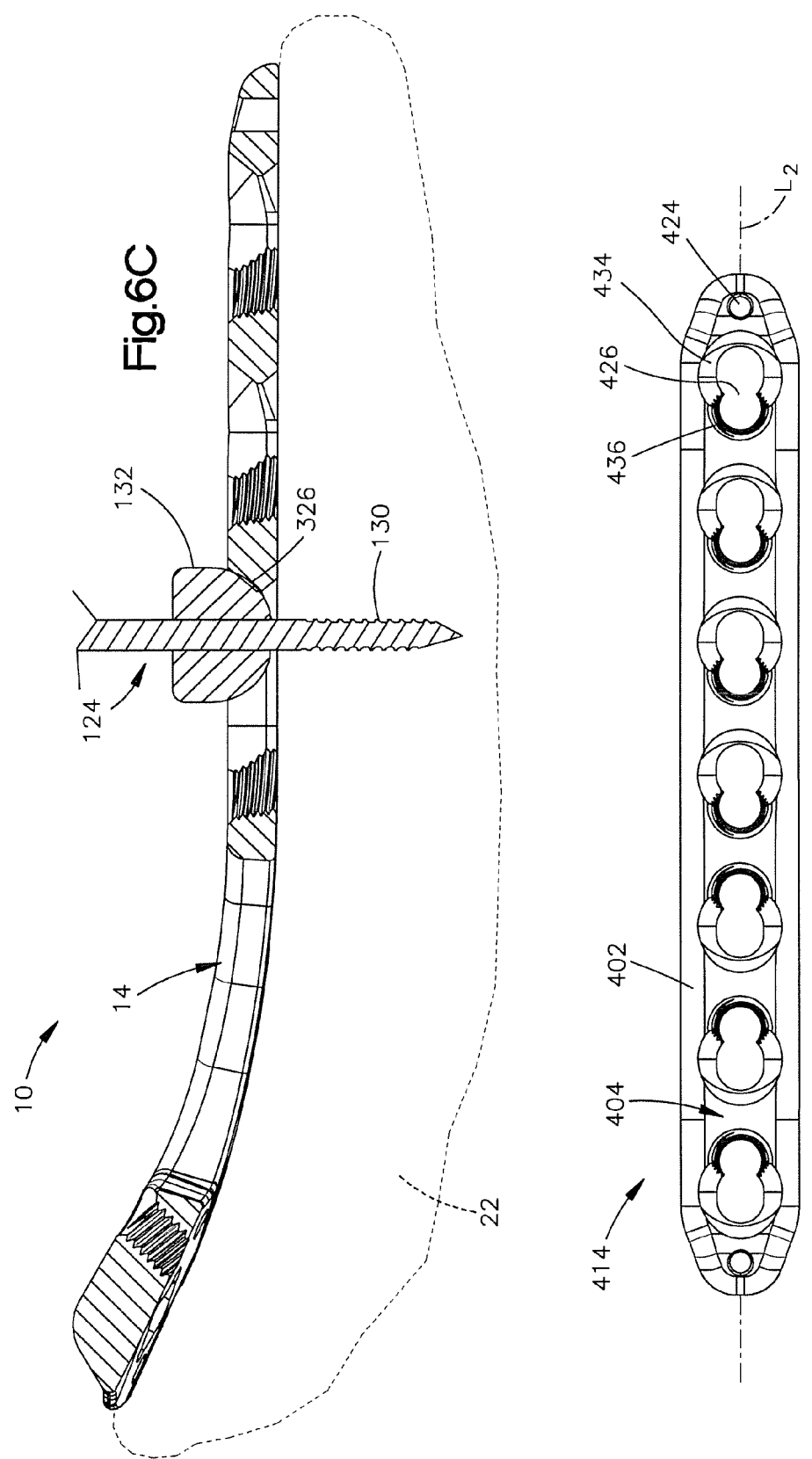

METHODS AND ASSEMBLIES FOR ALIGNING A BONE FIXATION PLATE

CROSS REFERENCE TO RELATED APPLICATIONS

This application claims the benefit of U.S. Provisional Patent Application No. 61/364,232, filed Jul. 14, 2010, the disclosure of which is hereby incorporated by reference as if set forth in its entirety herein.

BACKGROUND

A variety of fixation devices for the reduction of bone or bone fragments are well known. Some fractures, including wrist fractures, can be difficult to align and treat. Alignment and fixation have been typically performed by one of several methods, including casting, external fixation, and interosseous wiring. Casting is noninvasive, but may not be able to maintain alignment of the fracture where many bone fragments exist. Therefore, as an alternative, external fixators may be used. External fixators utilize a method known as ligamentotaxis, which provides distraction forces across the joint and permits the fracture to be aligned based upon the tension placed on the surrounding ligaments. However, while external fixators can maintain position, it may nevertheless be difficult in certain fractures to first properly align the bones. In addition, external fixators are often not suitable for fractures resulting in multiple bone fragments. In addition, external fixation is associated with reflex sympathetic dystrophy, stiffness, and pin complications. Moreover, with some fractures, movement helps to facilitate rehabilitation, and this movement is prevented by external fixation. Interosseous wiring is an invasive procedure whereby screws are positioned into the various fragments and the screws are then wired together as bracing. This is a difficult and time consuming procedure. Moreover, unless the bracing is quite complex, the fracture may not be properly stabilized.

As a result, fixation of fractures, including those of the wrist have more recently been performed using bone fixation plates. Attachment of a bone fixation plate to a fractured bone is accomplished by first reducing the fracture fragment(s) and subsequently attaching the bone fixation plate to the bone on opposite sides of the fracture site(s) using bone screws or the like. It is therefore important in many instances to ensure that the bone fixation plate is properly positioned on the bone to ensure that the bone fragment(s) are adequately reduced. Thus, the bone fixation plate is temporarily affixed to the bone, and a medical image (e.g., X-ray) determines whether the fracture site is adequately reduced before the bone fixation plate is permanently affixed to the bone.

Several systems are being used to temporarily affix a bone fixation plate to an underlying fracture bone to determine proper reduction prior to permanent plate fixation. For instance, in one system, a K-wire is screwed or otherwise driven through the screw holes of the plate on opposite sides of the fracture. The K-wire is smaller in diameter than the screw holes, and is thus positioned so as to bear against opposing edges of the respective screw holes so as to prevent movement of the plate during imaging. The process of accurately positioning the K-wire so as to prevent movement of the bone fixation plate has proven difficult and tedious, as any space between the K-wire and the outer edge of the screw hole will allow movement. In another system, holes are pre-drilled in the bone, and a cortex (e.g., non-locking) screw is inserted through the screw hole and into the pre-drilled hole in the bone. Unfortunately, several unnecessary holes are drilled in the bone as the bone fixation plate is repositioned. In yet another system, holding clamps attach to the bone fixation plate and are invasively fitted around the bone.

SUMMARY

In accordance with one embodiment, a bone fixation assembly includes a bone fixation plate having at least one first aperture, and at least one second aperture having a dimension greater than the at least one first aperture. The second aperture is configured to receive a bone screw having a screw shaft and a screw head. The bone fixation assembly further includes a temporary fixation wire having a proximal end, a distal end, and an abutment member disposed between the proximal and distal ends. The abutment member has a cross-sectional dimension greater than that of the distal end, and greater than that of at least a portion of one of the first and second apertures, such that a single temporary fixation wire can be inserted into one of the apertures, and the abutment member of the single temporary fixation wire temporarily compresses the bone fixation plate against the underlying bone to thereby prevent movement of the bone fixation plate relative to the bone prior to inserting any bone screws into the one or more second apertures.

In another embodiment, a bone fixation assembly includes a bone fixation plate having a plurality of apertures. At least some of the plurality of apertures are configured to receive respective bone fixation members, and at least one of the plurality of apertures includes an outer region and an inner region. The outer region having a cross-sectional dimension greater than that of the inner region. The assembly further includes a temporary fixation wire having a proximal end, a distal end, and an abutment member disposed between the proximal and distal ends. The abutment member has a cross-sectional dimension greater than that of the distal end and greater than that of the inner region of the at least one aperture such that when inserted into the at least one aperture, at least a portion of the abutment member is disposed within at least the outer region of the at least one aperture so as to temporarily compress the bone fixation plate against the underlying bone to thereby prevent movement of the bone fixation plate relative to the bone prior to inserting any fixation members into the apertures of the bone fixation plate.

In another embodiment, a bone fixation assembly includes a bone fixation plate defining at least one first aperture, and at least one second aperture having a cross-sectional dimension greater than a cross-sectional dimension of the at least one first aperture. The at least one second aperture is configured to receive a bone screw having a screw shaft and a screw head. The assembly further includes a temporary fixation wire including a proximal end, a distal end, and an abutment member disposed between the proximal and distal ends. The distal end has a cross-sectional dimension substantially equal to that of the at least one first aperture. The abutment member has a cross-sectional dimension greater than that of the distal end and greater than that of the at least one first aperture, such that when the temporary fixation wire is inserted into the at least one first aperture, the abutment member temporarily compresses the bone fixation plate against the underlying bone to thereby prevent movement of the bone fixation plate relative to the bone prior to inserting any bone screws into the apertures of the bone fixation plate.

A method of aligning and affixing a bone fixation plate to an underlying bone is also disclosed. The method includes aligning a bone fixation plate to an underlying bone, the bone fixation plate defining at least one first aperture, and at least one second aperture having a dimension greater than a dimension of the at least one first aperture. A temporary fixation wire having a wire body and an abutment member extending out from the wire body is inserted into one of the first and second apertures such that the abutment member compresses against the bone fixation plate and prevents movement of the bone fixation plate relative to the underlying bone. A permanent fixation member is then inserted into the at least one second aperture to thereby permanently affix the bone fixation plate to the underlying bone. The temporary fixation wire may then be removed.

BRIEF DESCRIPTION OF THE DRAWINGS

The foregoing summary, as well as the following detailed description of the preferred embodiments of the application, will be better understood when read in conjunction with the appended drawings. For the purposes of illustrating the bone fixation assembly, there are shown in the drawings preferred embodiments. It should be understood, however, that the application is not limited to the precise arrangements and instrumentalities illustrated in the drawings, in which:

FIG. 1 is a side perspective view of a bone fixation assembly including a bone fixation plate and a temporary fixation wire temporarily affixing the bone fixation plate to an underlying bone;

FIG. 2A is a perspective view of the temporary fixation wire shown in FIG. 1;

FIG. 2B is a side elevation view of the temporary fixation wire shown in FIG. 2A;

FIG. 3A is a perspective view of a temporary fixation wire constructed in accordance with an alternative embodiment;

FIG. 3B is a side elevation view of the temporary fixation wire shown in FIG. 3A;

FIG. 4A is a perspective view of a temporary fixation wire constructed in accordance with another alternative embodiment;

FIG. 4B is a side elevation view of the temporary fixation wire shown in FIG. 4A;

FIG. 6A is a side sectional view of a bone fixation assembly including the temporary fixation wire shown in FIG. 2A extending through a temporary fixation wire hole of the bone fixation plate shown in FIG. 5A;

FIG. 6B is a side sectional view of a bone fixation assembly including the temporary fixation wire shown in FIG. 3A extending through a temporary fixation wire hole of the bone fixation plate shown in FIG. 5A;

FIG. 6C is a side sectional view of a bone fixation assembly including the temporary fixation wire shown in FIG. 4A extending through a temporary fixation wire hole of the bone fixation plate shown in FIG. 5A; and FIG. 7 is a top plan view of a bone fixation plate constructed in accordance with an alternative embodiment, the bone fixation plate including a plurality of permanent bone fixation holes, and temporary fixation wire holes.

DETAILED DESCRIPTION

Figure 5A:
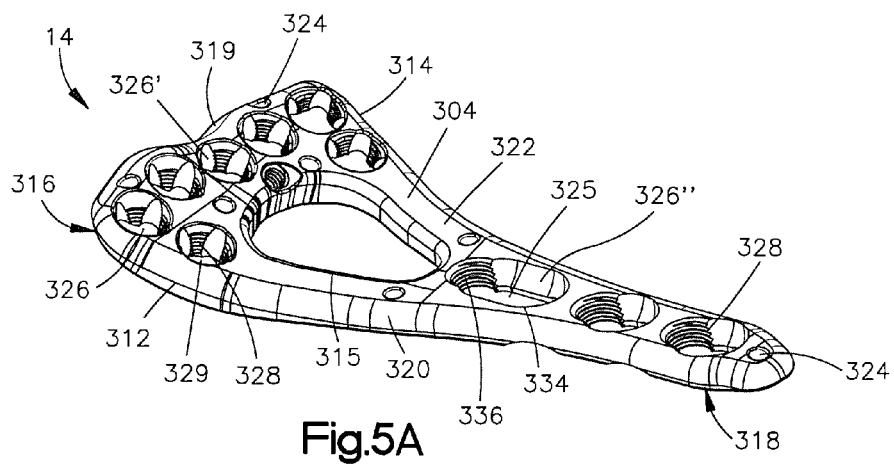
FIG. 5A is a perspective view of the bone fixation plate shown in FIG. 1, the bone fixation plate having a plurality of permanent bone fixation holes, and temporary fixation wire holes.

Referring to FIG. 1, a bone fixation assembly 10 includes a bone fixation plate 14, and one or more temporary fixation wires (such as temporary fixation wire 24) that temporarily fix the bone fixation plate 14 to an underlying bone 22, such as a radius as illustrated, so that the alignment of the bone fixation plate 14 can be examined. The bone fixation assembly 10 can further include a plurality of permanent bone fixation members 317, illustrated as screws, that can permanently attach the bone fixation plate 14 to the underlying bone 22 once the bone fixation plate 14 has been properly aligned. The term "permanently" is used herein as a duration of time sufficient to allow the bone fracture to heal. Thus, once the fracture has been repaired, the bone fixation plate 14 can be removed from the underlying bone 22 if desired.

The bone fixation plate 14, and the temporary fixation wires may be configured such that only a single temporary fixation wire may be inserted through the bone fixation plate 14 and into the underlying bone 22 to thereby temporarily prevent movement of the bone fixation plate 14 relative to the underlying bone 22. It should be understood, however, that more that one temporary fixation wire may be inserted through the bone fixation plate 14, and into the underlying bone 22, as desired. As will be described, the temporary fixation wire may be constructed in accordance with several embodiments.

Referring to FIGS. 2A and 2B, according to one embodiment a temporary fixation wire 24 includes a wire body 26 that is longitudinally elongate along a longitudinal axis L1. The temporary fixation wire 24 may be a stainless steel wire or any wire or ligature suitable for reduction of a bone fracture, and can have a length that extends along the longitudinal axis of any distance as desired, such as approximately 150 mm. The wire body 26 defines a proximal end 28 and an opposing distal end 30. The temporary fixation wire 24 includes an abutment member 32 that is attached to the wire body 26 and separates the distal end 30 from the proximal end 28. The proximal and distal ends 28 and 30 and the abutment member 32 can all be cylindrical in shape as illustrated, or can assume any suitable alternative shape as desired. The distal end 30 of the temporary fixation wire 24 defines a temporary fixation member 34 configured to be inserted into the underlying bone 22. The proximal end 28 of the temporary fixation wire 24 is configured to be engaged by an insertion tool.

As shown in FIGS. 2A and 2B, the temporary fixation member 34 includes helical threads 36 and a tapered or pointed driving end or tip 37 that can present one or more cutting flutes. In this regard, it should be appreciated that the temporary fixation member 34 can be self-tapping if desired. The tip 37 is thus configured to be driven into the underlying bone 22 to a depth such that rotation of the temporary fixation wire 24 causes the threads 36 to engage the bone as the temporary fixation wire 24 is driven into the bone 22. The threads 36 extend proximally from the tip 37 to a location distal of the abutment member 32. The threads 36 can extend to the abutment member 32, or can terminate at a location spaced distally from the abutment member 32. Accordingly, the temporary fixation wire 24 can be driven into underlying bone to a depth that causes the abutment member 32 to apply compression against the bone fixation plate 14.

The wire body 26 can be sized and shaped as desired, and in accordance with the illustrated embodiment is dimensioned such that the diameter or thickness of the proximal end 28 and the outer diameter or thickness of the threads 36 are both approximately 1.25 mm, though it should be appreciated that the diameter of the proximal end 28 and the outer diameter threads 36 can be sized as desired, for instance at approximately 1.6 mm, any distance between approximately 1.25 mm and approximately 1.6 mm, or any distance less than approximately 1.25 mm or greater than approximately 1.6 mm. In this regard, it should be appreciated that the outer diameter of the threads 36 can be substantially equal to, greater than, or less than the diameter of the proximal end 28. It should be appreciated throughout this disclosure while that various structure is illustrated as round or cylindrical, defining a diameter, that the structure can be alternatively shaped as desired, and thus unless otherwise indicated, the diameters of all structure described herein can alternatively be referred to as a cross-sectional dimension or thickness that extends along a transverse direction T that is perpendicular with respect to the longitudinal axis L1.

With continuing reference to FIGS. 2A and 2B, the abutment member 32 can be provided as an annular washer that is welded at both ends (for instance laser welded) onto the wire body 26 at a location proximal of the threads 36. Alternatively, the abutment member 32 can be attached to the wire body 26 using any suitable attachment, or can be constructed integrally with the wire body 26.

As shown in FIG. 2B, the abutment member 32 includes a proximal end 38 that defines a corresponding proximal surface 39 extending transversely out from the proximal end 28 of the wire body 26, and a distal end 40 that defines a distal surface 41 extending transversely out from the distal end 30 of the wire body 26. The distal surface 41 of the abutment member 32 can be spaced from the tip 37 any distance as desired, such as between approximately 5 mm and 15 mm. In particular the distal surface 41 can be spaced from the tip 37 by approximately 8 mm.

The abutment member 32 can further include an intermediate portion 42 that defines an intermediate surface 43 extending longitudinally between the proximal end 38 and the distal end 40. It should be appreciated that the proximal and distal surfaces 39 and 41 of the abutment member 32 can extend in a purely transverse direction, or in a direction having both transverse and longitudinal directional components. Likewise, it should be appreciated that the intermediate surface 43 can extend in a pure longitudinal direction, or in a direction having both longitudinal and transverse directional components.

In accordance with the embodiment illustrated in FIG. 2B, the abutment member 32 includes a tapered or curved interface 45 between the distal end 40 and the intermediate portion 42. The interface 45 is tapered such that the diameter of the abutment member 32 is reduced along a distal longitudinal direction from the intermediate surface 43 toward the distal surface 41. The interface 45 can be straight, curved, or can include a combination of straight and curved portions. The distal surface 41 can extend in a purely transverse direction, or can extend in a direction that includes both transverse and longitudinal directional components. The distal surface 41 and the interface 45 can be combined into a single continuous surface. As illustrated, the distal surface 41 defines a diameter less than that of the intermediate surface 43, and greater than that of the distal end 30 of the wire body 26. The intermediate surface 43 defines a diameter that is greater than the diameter of the distal end 30, and can further be greater than the diameter of the proximal end 28. In accordance with one embodiment, the intermediate section can define a diameter or cross-sectional dimension as desired, such as in the range of approximately 1.25 mm and approximately 2.5 mm, and in one embodiment is approximately 1.25 mm. It should thus be appreciated that the diameter of the intermediate surface 43 is greater than the outer diameter of the threads 36, and greater than the outer diameter of any unthreaded region that may exist, for instance, between the threads 36 and the abutment member 32.

Referring now to FIGS. 3A and 3B, a temporary fixation wire 124 in accordance with another embodiment is illustrated as including reference numerals corresponding to like structure of the temporary fixation wire 24 described above with respect to FIGS. 2A and 2B. Thus, unless otherwise indicated, the temporary fixation wire 124 is constructed substantially identically with respect to the temporary fixation wire 24. As illustrated, the temporary fixation wire 124 includes an abutment member 132 defining an intermediate surface 143 that has a diameter greater than that of the intermediate surface 43, and further has a diameter greater than its longitudinal length. For instance, the abutment member 132 can have a diameter (or transverse cross-sectional dimension) as desired, for instance between approximately 6.0 mm and 8.0 mm. The abutment member 132 defines a distal surface 141 that can be spaced from the tip 137 any distance as desired, such as between approximately 5 mm and 20 mm. In particular the distal surface 141 can be spaced from the tip 137 by approximately 8 mm.

Referring now to FIGS. 4A and 4B, a temporary fixation wire 224 according to another embodiment is illustrated as including reference numerals corresponding to like structure of the temporary fixation wire 124 described above with respect to FIGS. 3A and 3B incremented by 100. Thus, unless otherwise indicated, the temporary fixation wire 224 is constructed substantially identically with respect to the temporary fixation wire 124. As illustrated, the temporary fixation wire 224 includes an abutment member 232 that is bullet shaped, having a distal end 240 that is tapered inwardly along a distal direction. The abutment member defines a distal surface 241 that is convex with respect to a vantage point along the longitudinal direction L1 from the distal end 230 of the wire body 226, though the distal surface 241 could alternatively assume any shape as described above with respect to the distal surface 41. The proximal surface 239 is substantially flat in the transverse direction. The distal surface 241 of the abutment member 232 can be spaced from the tip 237 any distance as desired, such as between approximately 5 mm and 20 mm. In particular the distal surface 241 can be spaced from the tip 237 by approximately 8 mm.

Figure 5B:
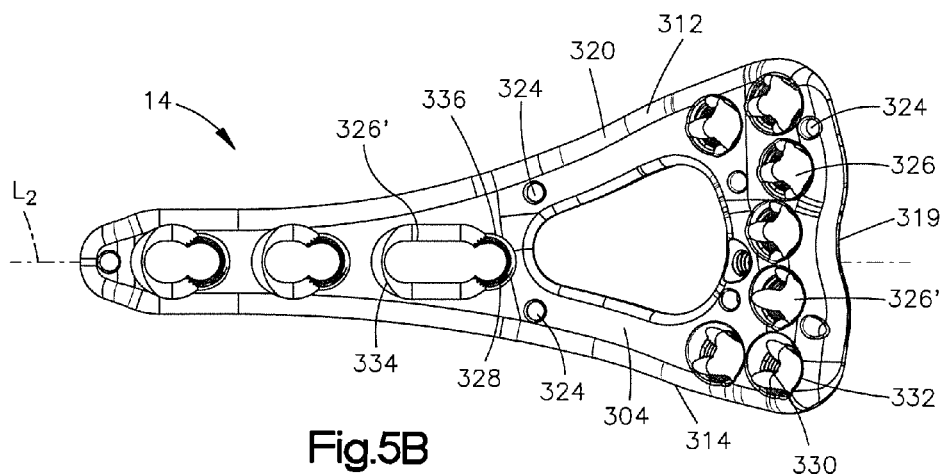
FIG. 5B is a top plan view of the bone fixation plate shown in FIG. 5A.
Figure 5C:
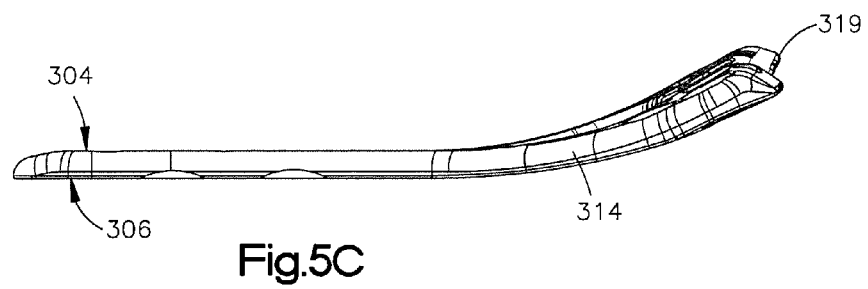
FIG. 5C is a side elevation view of the bone fixation plate shown in FIG. 5A.

As shown in FIGS. 5A-5C, the bone fixation plate 14 includes a body 302 having an upper surface 304 and an opposing bone contacting surface 306. When the bone fixation plate 14 is used to reduce a fracture of a long bone, such as a distal radius, the bone contacting surface 306 can be placed on a plate engaging surface, such as the volar surface of the distal radius. The body 302 includes a head portion 316 and a shaft portion 318 that extends proximally from the head portion 316 along a longitudinal axis L2. The bone fixation plate body 302 can include an opening 315 extending through the head portion 316 that separates the head portion 316 into a medial section 320 and a lateral section 322. The head portion 316 further includes a distal section 319 connected between the medial and lateral sections 320 and 322 at a location distal of the opening 315. The bone fixation plate body 302 thus defines a medial edge 312 and a lateral edge 314 that flare away from each other in a direction from the shaft portion toward the head portion 316, such that the head portion is sized and shaped to conform to the metaphysic of the distal radius.

It should be appreciated that the bone fixation plate 14 illustrated in FIGS. 5A-5C is configured to conform to the distal radius of a right arm, and that the bone fixation plate 14 can also be constructed to conform to the distal radius of the left arm. Furthermore, the bone fixation plate 14 has been described and illustrated in accordance with one embodiment, and the temporary fixation wires of the type described above are intended to be usable in combination with any bone fixation plate, for instance the bone fixation plate illustrated in FIG. 7, so as to temporarily align the bone fixation plate with fractured bone segments of any bone, such as for instance the tibia, fibula, or any other type of bone such as of the foot and hand, as desired prior to permanent bone plate fixation using permanent bone screws.

With continued reference to FIGS. 5A-5C, the bone fixation plate 14 defines a plurality of apertures extending through the bone fixation plate body 302. In particular, the bone fixation plate 14 includes a first plurality (or one or more) of small temporary fixation wire apertures 324 having a first diameter, and a second plurality of large temporary fixation wire apertures 326 having a second diameter greater than that of the first plurality of apertures 324. Both apertures 324 and 326 define a diameter that is greater than that of the wire body of any of the temporary fixation wires described above, and smaller than that of the corresponding abutment member. The apertures 324 can be sized to correspond to the smaller temporary fixation wire 24, while the apertures 326 can be sized to correspond to the larger temporary fixation wires 124 and 224. One or more of the apertures 324 and 326 can be disposed on the medial section 320 of the head, the lateral section 322 of the head, the distal section 319 of the head, or on the shaft 318.

The apertures 324 can thus extend through the shaft portion 318, the head portion 316, or at both the head and shaft portions. A pair of apertures 324 can be positioned in alignment at the opposed medial and lateral sections 320 and 322, and can also be positioned at the distal section 319. The diameter of the apertures 324 can be sized substantially equal to, or slightly greater than, that of the distal end 30 of the wire body 26, and less than that of the abutment member 32. Accordingly, as illustrated in FIG. 6A, the distal end of the wire body 26 can be inserted into one of the apertures 324 and driven (for instance screwed) into the underlying bone until the distal surface 41 of the abutment member 32 is brought against the upper surface 304 of the bone fixation plate body 302, thereby compressing the bone fixation plate body 302 against the bone and temporarily fixing the position of the bone fixation plate 14 on the bone. Furthermore, because the diameter of the distal end 30 corresponds to that of the aperture 324, the bone fixation plate 14 is unable to be translated relative to the temporary fixation wire 24 (and thus the underlying bone) once the temporary fixation wire 24 has been inserted into the aperture 324 and driven into the underlying bone.

If it is determined that the bone fixation plate 14 should be repositioned, the temporary fixation wire 24 can be removed from the underlying bone. Advantageously, the residual hole created in the bone from the temporary fixation wire is smaller than the residual hole that would be produced by a permanent bone fixation member used to temporarily fix the bone fixation plate 14 to the underlying bone. Once the bone fixation plate 14 has been repositioned, the temporary fixation wire 24 can again be inserted into the same aperture 324 or a different aperture 324 to again temporarily fix the position of the bone fixation plate 14. The plate 14 can be repositioned and temporarily fixed as many times as needed before it is determined that the plate 14 is accurately positioned, and can then be permanently affixed using permanent bone fixation members 317. Once the plate 14 has been affixed to the underlying bone with the bone permanent bone fixation member 317, the temporary fixation wire 24 can then be removed.

It should be appreciated that while the diameter of the apertures 324 is sized to receive the wire body 26, the diameter of the apertures 324 can also be sized substantially equal to, or slightly greater than, that of the distal ends 130 and 230 of the wire bodies 126 and 226 such that the temporary fixation wires 124 and 224 can be inserted into the apertures 324 to temporarily fix the position of the bone fixation plate 14 as described above with respect to the temporary fixation wire 24.

Now referring to FIGS. 5A-5C, 6B and 6C, the apertures 326 have a diameter greater than that of the distal ends of the temporary fixation wires 124 and 224, but smaller than that of the abutment members 132 and 232. The apertures 326 can include one or more apertures 326' that are substantially cylindrical, and one or more apertures 326" that are longitudinally elongate. Both types of apertures 326' and 326" are dimensioned so as to receive a permanent bone fixation member 317 therein. One or more, up to all, of the apertures 326 can include threads 328 that mate with complementary threads on the head of a permanent bone fixation member 317 as desired. The permanent bone fixation member 317 further includes a screw shaft 323 (which can be threaded) extending down from the head. The shaft 323 has a thickness that is perpendicular to the central axis of the permanent bone fixation member and passes through the central axis. The permanent bone fixation member 317 can have several distinguishing features with respect to a temporary fixation wire. For instance, the permanent fixation member 317 is intended to permanently affix the bone fixation plate 14 to the underlying bone. Moreover, the thickness of the shaft of the permanent bone fixation member 317 is greater than the thickness of the distal end of the temporary fixation wire. In one embodiment, the permanent bone fixation member 317 does not include a wire extending from the permanent bone fixation member head in an opposite direction of the permanent bone fixation member shaft 323. Furthermore, in one embodiment, the permanent bone fixation member head can be threaded as desired.

The threads 328 of the apertures 326' can be disposed on circumferentially spaced downwardly extending fingers 329, so that a permanent bone fixation member 317 having complementary threads on the screw head can be locked at variable angles inside the screw aperture 326'. Alternatively, the apertures 326' and 326" can be unthreaded, such that the screw head compresses the bone fixation plate body 302 against the underlying bone when the permanent bone fixation member 317 is driven into the underlying bone using any suitable driving tool. The cylindrical apertures 326' can include an upper or outer unthreaded region 330 and a lower or inner threaded region 332. The apertures 326' can be tapered inwardly along a direction from the upper surface 304 toward the bone-contacting surface 306, such that the threaded region 332 has a diameter less than that of the upper unthreaded region 330.

The upper end of the outer unthreaded region 330 of the apertures 326' can have a diameter that is greater than that of the distal surface of the abutment member of the corresponding temporary fixation wire, and the lower end of the outer unthreaded region 330 can have a diameter that is less than that of the distal surface of the abutment member of the corresponding temporary fixation wire. Accordingly, when the temporary fixation wire is inserted through one of the apertures 326', the abutment member 132 or 232 compresses against the upper unthreaded region 330, and not the threaded region 332 so as to avoid damaging the threads 328 of the threaded region 332. Because a portion of the abutment member has a diameter substantially equal to a portion of the unthreaded region 330, the bone fixation plate 14 is unable to be translated relative to the temporary fixation wire (and thus the underlying bone) once the temporary fixation wire has been inserted into the aperture 326' and driven into the underlying bone.

The apertures 326" are longitudinally elongate, and have a first portion 334 and a second portion 336. The first portion 334 is longitudinally elongate, and has a transverse dimension substantially equal to that of the head of a permanent bone fixation member 317 (and the abutment member of the complementary temporary fixation wire). The transverse dimension of the first portion 334 flares inwardly along a direction from the top surface 304 of the plate body 302 toward the bone contacting surface 306. Thus, the abutment member of the corresponding temporary fixation wire 124, 224 can nest in the first portion 334, and apply compression against the bone fixation plate 14 when driven into the underlying bone that prevents the bone fixation plate 14 from moving relative to the temporary fixation wire. The second portion 336 can be substantially cylindrical, having an open portion that is continuous with the first portion 334. The second portion 336 can be unthreaded or threaded in the manner described above, or can be threaded continuously from the upper surface 304 to the bone contacting surface 306, as the second portion 336 does not receive a temporary fixation wire.

Once the temporary fixation wire 124 or 224 has been inserted through one of the apertures 326 and driven sufficiently deep so as to compress the plate 14 against the underlying bone, the alignment of the bone fixation plate 14 can be determined using X-ray or other suitable imaging. If it is determined that the bone fixation plate 14 should be repositioned, the temporary fixation wire 124, 224 can be removed from the underlying bone. Advantageously, the residual hole created in the bone is reduced with respect to the hole that would have remained if a permanent bone fixation member were used to temporarily fix the plate 14 to the underlying bone instead of the temporary fixation wire. Once the bone fixation plate 14 has been repositioned, the temporary fixation wire can again be inserted into the same aperture 326' or a different aperture 326' to again temporarily fix the position of the bone fixation plate 14. The plate 14 can be repositioned and temporarily fixed as many times as needed before it is determined that the plate 14 is accurately positioned, and can then be permanently affixed using bone screws 317. Once the plate 14 has been affixed to the underlying bone with the bone permanent bone fixation member, the temporary fixation wire can then be removed.

It should be appreciated that the diameter of the apertures 326', or transverse dimension of the apertures 326" can be sized greater than that of the abutment member 32 such that the wire 24 is not able to be used with the apertures 326. If one were to attempt to temporary fix the bone fixation plate 14 to the underlying bone using the wire 24, the diameter of the abutment member 32 would be visibly smaller than that of the apertures 326', and the transverse dimension of the apertures 326", and thus too small to provide compression against the plate 14.

It should be further appreciated that a kit can be provided that includes one or more bone fixation plates 14, or one or more temporary fixation wires 24, 124, 224, or one or more bone screws 317, or alternatively constructed plates and temporary fixation wires, or a combination of any or all of the same. Advantageously, the bone fixation plate 14 can be temporarily fixed against the bone using a single temporary fixation wire 24, 124, or 224. Furthermore, the installation of the temporary fixation wire does not prevent one or more bone screws from permanently affixing the bone fixation plate 14 to the underlying bone.

While the underlying bone has been illustrated as a wrist in FIGS. 6A-6C, such that the bone fixation plate 14 is sized and shaped to conform to the wrist, the bone fixation plate can be alternatively constructed as desired so as to conform to any underlying bone as desired. For instance, referring now to FIG. 7, a bone fixation plate 414 is illustrated having reference numerals corresponding to like elements of the bone plate 14 incremented by 100 for the purposes of form and clarity. The bone fixation plate 414 includes a body 402 having an upper surface 404 and an opposed bone contacting lower surface. When the bone fixation plate 14 is used to reduce a fracture of a long bone, such as a distal radius, the bone contacting surface can be placed on a plate engaging surface of the underlying bone. The plate body 402 extends substantially linearly along the central axis L2, and can be configured to be fixed onto a long bone The bone fixation plate 414 defines a plurality of apertures extending through the bone fixation plate body 402. In particular, the bone fixation plate 414 is illustrated as including a first plurality of small temporary fixation wire apertures 424, and a second plurality of large fixation wire apertures 426 each including a first portion 434 and a second portion 436 extending through the plate body 402. The portions 434 and 436 are open to each other along the central axis L2 of the bone plate 414. As described above, the distal end of a temporary wire body can be inserted into one of the aperture portions 424 and 426 of the plate body 402 and driven (for instance screwed) into the underlying bone until the distal surface of the abutment member is brought against the upper surface 404 of the bone fixation plate body 402, thereby compressing the bone fixation plate body 402 against the bone and temporarily fixing the position of the bone fixation plate 414 on the bone. Furthermore, because the diameter of the distal end of the temporary fixation wire corresponds to that of the aperture into which the temporary fixation wire 24 is inserted, the bone fixation plate 414 is unable to be translated relative to the temporary fixation wire (and thus the underlying bone) once the temporary fixation wire has been inserted into the aperture and driven into the underlying bone. Once the plate 414 has achieved proper alignment and has been permanently affixed to the underlying bone with the bone screws, the temporary fixation wire 24 can then be removed.

Although the invention has been described with reference to preferred embodiments or preferred methods, it is understood that the words which have been used herein are words of description and illustration, rather than words of limitation. For instance, it should be appreciated that the structures and features of the bone fixation plates and temporary fixation wires can be used in combination with other temporary fixation wires and bone fixation plates, respectively, unless otherwise indicated. Furthermore, although the invention has been described herein with reference to particular structure, methods, and embodiments, the invention is not intended to be limited to the particulars disclosed herein, as the invention extends to all structures, methods and uses that are within the scope of the present invention. The features of various embodiments described herein can further be incorporated into the other embodiments described herein as desired. Those skilled in the relevant art, having the benefit of the teachings of this specification, may effect numerous modifications to the invention as described herein, and changes may be made without departing from the scope and spirit of the invention.

What is claimed:

1. A bone fixation assembly comprising:
a bone fixation plate defining at least two apertures, each aperture including an outer region and an inner region, the outer regions defining a cross-sectional dimension that is greater than a cross-sectional dimension of the inner regions;
at least one permanent bone fixation member that is configured to be driven through one of the apertures so as to permanently affix the bone fixation plate to an underlying bone;
a temporary fixation wire that is elongate along a first direction, the temporary fixation wire including a wire body that has a thickness less than the thickness of the permanent bone fixation member, the temporary fixation wire further including an abutment member that extends from the wire body such that the abutment member defines a distal surface that extends out from the wire body along a second direction that is perpendicular to the first direction, a proximal surface that extends out from the wire body, and an intermediate surface that extends from the proximal surface toward the distal surface, the intermediate surface having a cross-sectional dimension that is equal to the cross-sectional dimension of the outer regions,
wherein insertion of the temporary fixation wire through the bone fixation plate causes the abutment member to temporarily compress the bone fixation plate against the underlying bone, such that the temporary fixation wire prevents movement of the bone fixation plate relative to the underlying bone prior to subsequent permanent fixation of the bone fixation plate to the underlying bone.

2. The bone fixation assembly of claim 1, wherein a distal end of the wire body is threaded.

3. The bone fixation assembly of claim 1, wherein a distal end of the wire body defines a tip and the abutment member defines a distal surface that is spaced apart from the tip by a distance between about 5 mm and about 15 mm.

4. The bone fixation assembly of claim 1, wherein the abutment member defines a tapered interface between the distal surface and the intermediate surface.

5. The bone fixation assembly of claim 4, wherein the tapered interface is curved.

6. The bone fixation assembly of claim 4, wherein the abutment member is bullet shaped.

7. The bone fixation assembly of claim 1, wherein a distance between the proximal surface and the distal surface is less than the thickness of the abutment member.

8. The bone fixation assembly of claim 1, wherein the thickness is a diameter.

9. The bone fixation assembly of claim 1, wherein the at least two apertures are first apertures, the bone fixation plate further defining at least one second aperture wherein the at least one second aperture of the bone fixation plate has a cross-sectional diameter that is substantially equal to a cross-sectional diameter of a distal end of the wire body.

10. The bone fixation assembly of claim 1, wherein at least one of the at least two apertures is longitudinally elongate and defines a first portion and a second portion.

11. The bone fixation assembly of claim 10, wherein the first portion is longitudinally elongate and is configured to receive the temporary fixation wire.

12. The bone fixation assembly of claim 1, wherein the outer regions are unthreaded and the inner regions are threaded, the outer unthreaded regions having a cross-sectional diameter that is substantially equal to that of a distal surface of the abutment member.

13. The bone fixation assembly of claim 12, wherein the bone fixation plate defines an upper surface and an opposing bone-contacting surface, the apertures being tapered along a direction from the upper surface toward the bone-contacting surface, such that the inner threaded region has a cross-section diameter that is less than that of the outer unthreaded region.

14. The bone fixation assembly of claim 1, wherein the bone fixation plate includes a head portion and a shaft portion, and defines a medial edge and a lateral edge that flare away from each other in a direction from the shaft portion toward the head portion.

15. The bone fixation assembly of claim 1, wherein the bone fixation plate is configured to be affixed to a volar surface of a distal radius.

16. A bone fixation assembly comprising:
a bone fixation plate defining an inner bone-facing surface and an opposed outer surface spaced from the inner surface in a first direction, the bone fixation plate including a plurality of apertures that extend through the inner and outer surfaces, at least some of the plurality of apertures configured to receive respective permanent bone fixation members, wherein at least one of the plurality of apertures that is configured to receive a respective permanent bone fixation member is elongate along a second direction that is perpendicular to the first direction, the at least one aperture defines a first threaded portion extending between the inner and outer surfaces and a second unthreaded portion spaced from the first threaded portion along the second direction;
at least one permanent bone fixation member that is configured to be driven through one of the apertures configured to receive a respective permanent bone fixation member and into an underlying bone so as to permanently affix the bone fixation plate to the underlying bone; and
a temporary fixation wire including a wire body and an abutment member that extends out from the wire body, wherein the abutment member has a cross-sectional dimension greater than that of the wire body, and greater than that of the second unthreaded portion of the at least one aperture along a third direction that is perpendicular to both the first and second directions such that when the temporary fixation wire is inserted into the second unthreaded portion of the at least one aperture, at least a portion of the abutment member compresses against only the second unthreaded portion so as to temporarily compress the bone fixation plate against an underlying bone to thereby prevent movement of the bone fixation plate relative to the underlying bone without contacting the first threaded portion.

17. The bone fixation assembly of claim 16, wherein a distal end of the wire body is threaded.

18. The bone fixation assembly of claim 16, wherein a distal end of the wire body defines a tip and the abutment member defines a distal surface that is spaced apart from the tip by a distance between about 5 mm and about 15 mm.

19. The bone fixation assembly of claim 16, wherein the abutment member defines a distal surface, an intermediate surface, and a tapered interface between the distal surface and the intermediate surface.

20. The bone fixation assembly of claim 19, wherein the tapered interface is curved.

21. The bone fixation assembly of claim 19, wherein the abutment member is bullet shaped.

22. The bone fixation assembly of claim 16, wherein the abutment member defines a proximal surface and a distal surface, and the distance between the proximal surface and the distal surface is less than the cross-sectional dimension of the abutment member.

23. The bone fixation assembly of claim 16, wherein the cross-sectional dimension of the abutment member is a diameter.

24. The bone fixation assembly of claim 16, wherein the aperture through which the permanent bone fixation member is to be driven through is configured as a locking hole.

25. A bone fixation assembly comprising:
  a bone fixation plate defining a bone-facing surface and an opposed outer surface, the bone fixation plate defining at least one first aperture and at least one second aperture that has a cross-sectional dimension greater than that of the at least one first aperture, the second aperture configured to receive a permanent bone fixation member; and
  a temporary fixation wire including a wire body that is elongate along a first direction, the temporary fixation wire further including an abutment member that extends out from the wire body and has a cross-section dimension greater than that of the wire body such that the abutment member (i) defines a proximal surface and a flat distal surface, and (ii) separates the wire body into a distal portion that extends out from the distal surface of the abutment member along the first direction and a proximal portion that extends out from the proximal surface of the abutment member along the first direction, wherein the distal portion of the wire body has a cross-sectional dimension substantially equal to that of the at least one first aperture-such that when the distal portion of the temporary fixation wire is inserted through the at least one first aperture, the distal surface of the abutment member temporarily abuts the outer surface so as to compress the bone fixation plate against an underlying bone and prevents movement of the bone fixation plate relative to the underlying bone.

26. The bone fixation assembly of claim 25, wherein a distal end of the wire body is threaded.

27. The bone fixation assembly of claim 25, wherein a distal end of the wire body defines a tip and the distal surface is spaced apart from the tip by a distance between about 5 mm and about 15 mm.

28. The bone fixation assembly of claim 25, wherein the abutment member further defines an intermediate surface and a tapered interface between the distal surface and the intermediate surface.

29. The bone fixation assembly of claim 28, wherein the tapered interface is curved.

30. The bone fixation assembly of claim 25, wherein a distance between the proximal surface and the distal surface is less than the cross-sectional dimension of the abutment member.

31. The bone fixation assembly of claim 25, wherein the cross-sectional dimension of the abutment member is a diameter.

32. The bone fixation assembly of claim 25, wherein the at least one second aperture of the bone fixation plate is longitudinally elongate and defines a first portion and a second portion.

33. A method of affixing a bone fixation plate to an underlying bone, the method comprising:
  aligning a bone fixation plate with an underlying bone, the bone fixation plate defining a plurality of apertures, at least one of the plurality of apertures each including an unthreaded outer region and a threaded inner region, the unthreaded outer region defining a cross-sectional dimension that is greater than that of the inner region;
  positioning a temporary fixation wire proximate a first aperture of the plurality of apertures, the temporary fixation wire including a wire body that is elongate along a first direction, and an abutment member that extends out from the wire body along a direction that is transverse to the first direction such that the abutment member (i) defines a proximal surface and a flat distal surface, and (ii) separates the wire body into a distal portion that extends out from the distal surface of the abutment member along the first direction and a proximal portion that extends out from the proximal surface of the abutment member along the first direction;
  inserting the temporary fixation wire into the first aperture such that the flat distal surface compresses against only the unthreaded outer region to thereby prevent movement of the bone fixation plate relative to the underlying bone without contacting the threaded inner region;
  inserting a permanent fixation member into another aperture of the plurality of apertures to thereby permanently affix the bone fixation plate to the underlying bone; and
  removing the temporary fixation wire from the first aperture.

34. The method of claim 33, wherein the inserting step comprises inserting the permanent fixation member into another aperture having the inner and outer regions such that a threaded head of the permanent fixation member mates with the threaded inner region of the another aperture.

* * * * *